US00PP27413P2

(12) United States Plant Patent
Probst

(10) Patent No.: US PP27,413 P2
(45) Date of Patent: Nov. 22, 2016

(54) ***COREOPSIS* PLANT NAMED 'STARBRIGHT'**

(50) Latin Name: ***Coreopsis* hybrid**
Varietal Denomination: Starbright

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 14/756,237

(22) Filed: Aug. 19, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Annette Para
(74) *Attorney, Agent, or Firm* — Penny J. Aguirre

(57) ABSTRACT

A new cultivar of hybrid *Coreopsis* named 'Starbright' that is characterized by its compact plant habit, its nearly sterile florets result in a floriferous and long bloom season that does not require deadheading with bloom commencing in mid June and lasting until hard frost in Connecticut, its very large inflorescences with ray florets that are light yellow in color with a maroon eye zone, its cold hardiness at least to U.S.D.A. Zone 5, and its resistance to powdery mildew and leaf spot.

2 Drawing Sheets

Botanical classification: *Coreopsis* hybrid.
Variety denomination: 'Starbright'.

BACKGROUND OF THE INVENTION

The present invention relates to a new and distinct cultivar of *Coreopsis* plant, botanically of hybrid origin and known as *Coreopsis* 'Starbright' and will be referred to hereinafter by its cultivar name, 'Starbright'. The new cultivar of *Coreopsis* is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop long-lived cultivars in a wide range of flower colors and plant forms that have sturdy plant habits, exhibit a true perennial habit, and are cold hardy to at least U.S.D.A Zone 5.

The new cultivar arose from a cross made by the Inventor in August of 2010 in his test garden in Hubbardston, Mass. between an unnamed, proprietary plant in the Inventor's breeding program, reference no. 11 09-22 (not patented), as the female parent and pollen that was pooled from a variety of unnamed, proprietary plants (not patented) from his breeding program as the male parent (all nearly sterile). The exact male parentage is therefore unknown. 'Starbright' was selected in September 2011 as a single unique plant amongst the resulting seedlings.

Asexual propagation of the new cultivar was first accomplished by stem cuttings under the direction of the Inventor in Kensington, Conn. in September of 2011. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar.

These attributes in combination distinguish 'Starbright' as a new and distinct cultivar of *Coreopsis*.

1. 'Starbright' exhibits a compact plant habit reaching an average of 38 cm in height and 45 cm in width.
2. 'Starbright' is nearly sterile and exhibits a floriferous and long bloom season that does not require deadheading, blooming commences in mid June and lasts until hard frost in Kensington, Conn.
3. 'Starbright' exhibits very large inflorescences with ray florets that are light yellow in color with a maroon eye zone.
4. 'Starbright' exhibits cold hardiness at least to U.S.D.A. Zone 5.
5. 'Starbright' exhibits resistance to powdery mildew and leafspot.

The female parent of 'Starbright' differs from 'Starbright' in having inflorescences with ray florets that are tubular in shape and in being very fertile causing it to stop producing inflorescences due to seed set. 'Starbright' can be most closely compared to the *Coreopsis* cultivars 'Cosmic Eye' (U.S. Plant Pat. No. 22,601) and 'Full Moon' (U.S. Plant Pat. No. 19,364). 'Cosmic Eye' is similar to 'Starbright' in being resistant to powdery mildew and leaf spot, in having flowers that are yellow in color with an eye zone, and in having a long bloom season that does not require deadheading. 'Cosmic Eye' differs from 'Starbright' in being shorter in height and in having inflorescences with less ray florets that are darker yellow in color. 'Full Moon' is similar to 'Starbright' in having inflorescences with ray florets that are light yellow in color. 'Full Moon' differs from 'Starbright' in having inflorescences with less ray florets per inflorescence that are solid yellow in color and in having a more open, less dense plant habit.

BRIEF DESCRIPTION OF THE DRAWINGS

The accompanying colored photographs illustrate the overall appearance and distinct characteristics of the new

*Coreopsis*. The photographs were taken of a three month-old plant (from a 30-cell plug) of 'Starbright' as grown outdoors in a two-gallon container in Cheshire, Conn.

Figure 1:
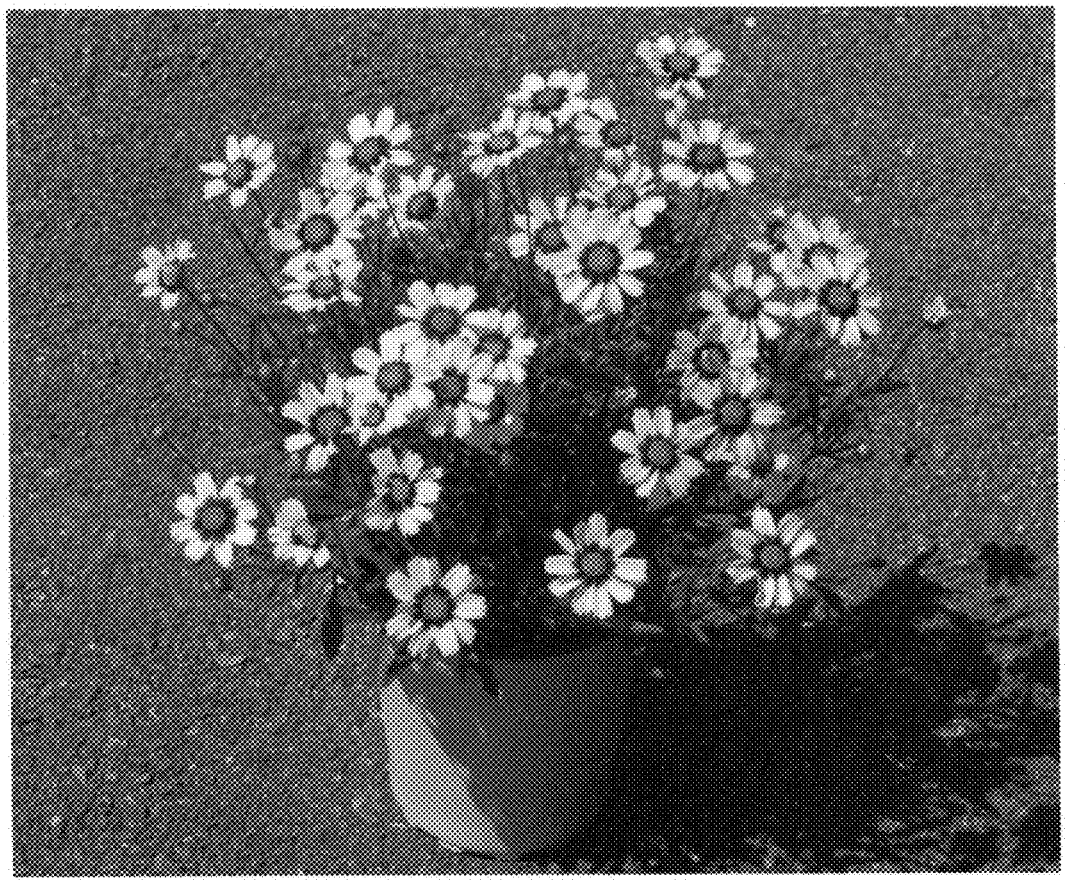

The photograph in FIG. 1 provides a view of 'Starbright' in bloom.

Figure 2:
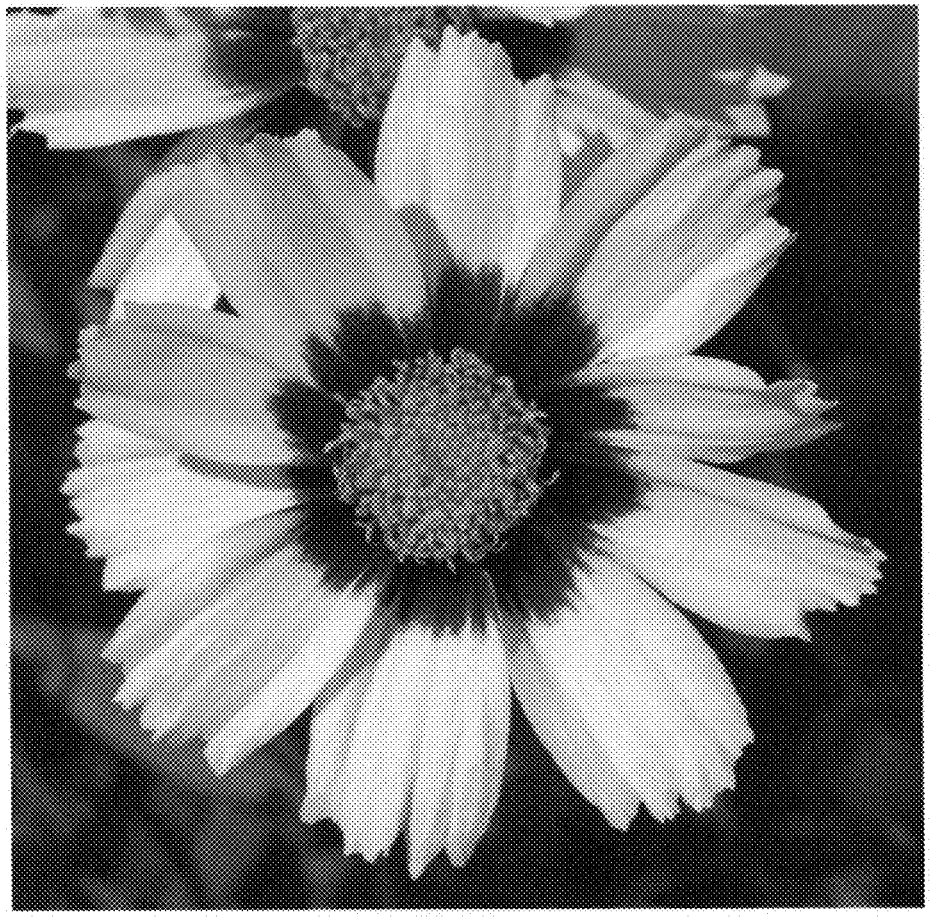

The photograph in FIG. 2 provides a close-up view of an inflorescence of 'Starbright'.

The colors in the photographs are as close as possible with the digital photography techniques available, the color values cited in the detailed botanical description accurately describe the colors of the new *Coreopsis*.

DETAILED BOTANICAL DESCRIPTION

The following is a detailed description of plants of the new cultivar three months in age as grown outdoors in two-gallon containers from 30-cell plugs in Cheshire, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from mid June until hard frost in Kensington, Conn.

*Plant type*.—Herbaceous perennial.

*Plant habit*.—Compact, clump-forming, densely branched above ground with stems that spread outward.

*Height and spread*.—An average of 38 cm in height and 45 cm in width as a one year-old plant in the landscape.

*Cold hardiness*.—At least in U.S.D.A Zone 5.

*Diseases resistance*.—Has been observed to be highly resistant to powdery mildew caused by *Podosphaera macularis* and leaf spot caused by *Pseudomonas cichorii*.

*Root description*.—Fibrous when young, becoming more fleshy with age, 199B in color.

*Propagation*.—Stem cuttings.

*Growth rate*.—Vigorous.

*Root development*.—Roots initiate in 6 to 8 days and fully develop in a 128-cell plug in about 28 days with bottom heat and rooting hormone at optimal times of the year.

Stem description:

*Shape*.—Round, solid.

*Stem color*.—Young and mature; 137B, woody base is a blend of 162D and N199B.

*Stem size*.—Main stems (excluding peduncles) average of 20 cm in length and 3 mm in width, lateral branches up to 11.5 cm in length (excluding peduncles) and 2.5 mm in width, secondary branches up to 2.5 cm in length and 2 mm in width.

*Stem surface*.—Young; glabrous, mature; ridged, dull and very slightly pubescent.

*Branching habit*.—An average of 10 main branches, each with 2 lateral branches with an average of 2 secondary branches per lateral branch.

*Internode length*.—Variable, 3 to 6 cm.

Foliage description:

*Leaf division*.—Simple or trifid.

*Leaf margins*.—Entire with short hairs.

*Leaf size*.—Up to 6 cm in length and 3.5 cm in width when trifid and up to 6 cm in length and 1.3 cm in width when simple.

*Leaf shape*.—Lobes of trifid lanceolate-oblong, lanceolate when simple.

*Leaf base*.—Truncate when trifid and attenuate when simple.

*Leaf apex*.—Acute.

*Leaf venation*.—Pinnate, inconspicuous, coloration same as leaf on both surfaces.

*Leaf attachment*.—Sessile.

*Leaf arrangement*.—Opposite.

*Leaf surface*.—Young and mature upper and lower surfaces are dull and very slightly puberulent.

*Leaf color*.—Young and mature upper surface; 137A, young and mature lower surface; 137B.

Flower description:

*Inflorescence type*.—Composite with ray florets surrounding disk florets in the center, forming a radiant head, inflorescences are borne on terminals arising from leaf axils.

*Lastingness of inflorescence*.—About 10 days until senescence of ray flowers, bracts and disk flowers are persistent.

*Fragrance*.—Light fragrance.

*Quantity of inflorescences*.—An average of 9 buds or open flowers per main stem at one time, blooms are continuously produced until frost.

*Inflorescence size*.—Up to 1.3 cm in depth and 4.7 cm in diameter with disk portion up to 1.3 cm in diameter.

*Inflorescence buds*.—An average of 9 mm in depth and 1.4 cm in diameter, shape is spherical, color N144A at apex and 138A at base.

*Peduncles*.—Strong, 5 to 12 cm in length when flower opens and 2 mm in diameter, 137B in color, surface is dull and very slightly pubescent.

Involucral bracts:

*Bract number*.—Two rows of 8.

*Bract arrangement*.—Outer bracts; free and held upright at about a 45° angle, inner bracts, lower half forms a cup under inflorescence with upper half of bracts free and held horizontal.

*Bract size*.—Outer; 1 cm in length and 4 mm in width, inner; 1.2 cm in length and 7 mm in width.

*Bract color*.—Outer; 137B on both surface, inner; translucent, 144A at apex and 138A at base on both surfaces.

*Bract texture*.—Outer; both surfaces slightly pubescent, inner glabrous and translucent.

*Bract apex*.—Outer; acuminate, inner; acute.

*Bract base*.—Truncate on inner and outer.

*Bract margins*.—Entire.

*Bract shape*.—Outer; lanceolate, inner; ovate.

Ray florets (sterile):

*Number*.—Average of 10.

*Shape*.—Oblong, appearance of three longitudinal sections with center section occasionally longer, slightly overlapping.

*Size*.—An average of 2 cm in length and 1 cm in width.

*Apex*.—3-lobed with lobes emarginate.

*Base*.—Cuneate.

*Margins*.—Entire on sides, lobed and emarginate at apex.

*Aspect*.—Held primarily horizontal.

*Texture*.—Both surfaces glabrous.

*Color*.—When opening and fully open upper surface; a color between 2A and 2B with base 59A, when opening and fully open lower surface; a color between 2A and 2B with base suffused with 187B.

Disk florets (perfect):

*Number*.—An average of 120.

*Shape*.—Tubular, corolla is fused and very slightly flared at apex.

*Size*.—An average of 1 cm in length and 1 mm in width.

*Color*.—En masse; 14A with spots of 166A, corolla (tube); base (tube) is 2A in color and translucent, flared portion is 4A and translucent.

*Receptacle*.—About 4 mm in diameter and 2.5 mm in depth, 144D in color.

Reproductive organs:

*Presence*.—Disk flowers are perfect, ray flowers are sterile.

*Gynoecium*.—1 Pistil, 4 mm in length, style is very fine and about 4A in color and translucent, stigma is bifid, pilose, 14A in color with branches about 1 mm in length and recurved, ovary is 1.5 mm in length, 1 mm in width, inferior, and 144C in color.

*Androcoecium*.—5 stamens, fused into tube surrounding style, 1 mm in length and 0.5 mm in width, 166A in color, no pollen was observed.

*Fruit/seed*.—No fruit or seed development was observed, plants have been observed to be nearly sterile.

It is claimed:

1. A new and distinct cultivar of *Coreopsis* plant named 'Starbright' as herein illustrated and described.

* * * * *